United States Patent [19]

McGovren et al.

[11] Patent Number: 5,087,639
[45] Date of Patent: Feb. 11, 1992

[54] PREVENTING CNS TOXICITY OF ACIVICIN WHEN USED WITH FOUR LARGE NEUTRAL AMINO ACIDS

[75] Inventors: J. Patrick McGovren, Schoolcraft Township, Kalamazoo County; Marta G. Williams, Prairieville Township, Allegan County; Robert H. Earhart, Richland Township, Kalamazoo County, all of Mich.

[73] Assignee: The Upjohn Company, Kalamazoo, Mich.

[21] Appl. No.: 266,437

[22] Filed: Nov. 2, 1988

[51] Int. Cl.$^5$ .......................................... A61K 31/195
[52] U.S. Cl. ................................................... 514/561
[58] Field of Search ........................................ 514/561

[56] References Cited

PUBLICATIONS

Peng et al, *J. Nutrition,* 103:607–17, 1973, "Food Intake Regulation: Amino Acid Toxicity and Changes in Rat Brain and Plasma Amino Acids".
McGovren et al, Proceedings of AACR, vol. 27, p. 1671, Mar. 1986, "Prevention of Acivicin-Induced CNS Toxicity by Concomitant Amino Acid Infusion".

*Primary Examiner*—Stanley J. Friedman
*Attorney, Agent, or Firm*—Sidney B. Williams, Jr.

[57] ABSTRACT

A method for the prevention of central nervous system toxicity of acivicin which comprises the concomitant administration of acivicin and an amino acid solution consisting essentially of large neutral amino acids.

15 Claims, 1 Drawing Sheet

PREVENTING CNS TOXICITY OF ACIVICIN WHEN USED WITH FOUR LARGE NEUTRAL AMINO ACIDS

FIELD OF INVENTION

This present invention provides a method for the prevention of central nervous system (CNS) toxicity of the anti-cancer agent (αS,5S)-α-amino-3-chloro-2-isoxazoline-5-acetic acid (ACIVICIN).

BACKGROUND OF THE INVENTION

ACIVICIN, a fermentation product of *Streptomyces sviceus* is an amino acid anti-cancer agent. ACIVICIN and the microbiological process for producing it are claimed in U.S. Pat. Nos. 3,856,807 and 3,878,047. A complete chemical synthesis of it is described in U.S. Pat. No. Re. 31,578. In humans it causes reversible, dose-limiting CNS effects such as sedation, ataxia, personality changes and hallucinations. These effects limit the maximum dose of acivicin in cancer patients.

In the cat, a species that exhibits some of the acivicin-induced CNS symptoms experienced by humans, it has been shown that an infusion of Aminosyn, 10% ® (a mixture of 16 amino acids), prior and subsequent to i.p. treatment with acivicin, prevented symptoms of drug-induced CNS toxicity and lowered the brain levels of acivicin to 15%-20% of controls, effects presumably due to blockage of drug-uptake into the brain by the increased plasma levels of amino acids. Aminosyn infusion also increased the total clearance of acivicin by ca. two-fold, resulting in lower drug levels in other tissues but not to the extent occurring in brain. Aminosyn administration did not block the anti-tumor efficacy of acivicin in mice bearing either L1210 leukemia or MX-1 human mammary carcinoma xenografts.

Infusion of an amino acid solution composed of alanine, arginine, histidine, proline, serine, typrosine and glycine (none of which are large neutral amino acids) was ineffective at preventing acivicin-induced CNS toxicity in the cat.

INFORMATION DISCLOSURE

Studies have shown that inhibition of amino acid transport into the brain is highest after ingestion of diets containing amino acids that are transported by the same system, Peng et al, *J. Nutrition*, 103:608-17, 1973.

The prevention of acivicin-induced CNS toxicity by concomitant amino acid infusion has been described by McGovren et al, Proceedings of AACR, Vol. 27, page 1671, March 1986. The amino acids utilized was Aminosyn ®, a mixture of essential amino acids, non-essential amino acids and electrolytes.

SUMMARY OF THE INVENTION

This invention provides: a method for the prevention of CNS, toxicity of acivicin in animals, including humans, which comprises the concomitant administration of acivicin and an amino acid solution consisting essentially of large neutral amino acids.

The advantage of using a solution of large neutral amino acids rather than a mixture of amino acids such as Aminosyn is (1) a decreased nitrogen load (important in patients with compromised liver or kidney function, (2) decreased electrolyte and osmolar load and (3) potentially lower fluid load (electrolyte and fluid loads are important in patients with potential cardiac dysfunction) and (4) probable ability to achieve more effective CNS protection because these advantages permit larger amounts of the amino acid to be given.

The time of administration of amino acid relative to acivicin given intravenously or orally is started from 30 minutes to eight hours prior to acivicin administration and continuing for eight hours to seven days after.

A large neutral amino acid solution means a solution containing one or any combination of the following large neutral amino acids: valine, leucine, isoleucine or phenylalanine at concentrations of 100 to 1000 mg/ml.

DESCRIPTION OF THE PREFERRED EMBODIMENT

Figure 1:
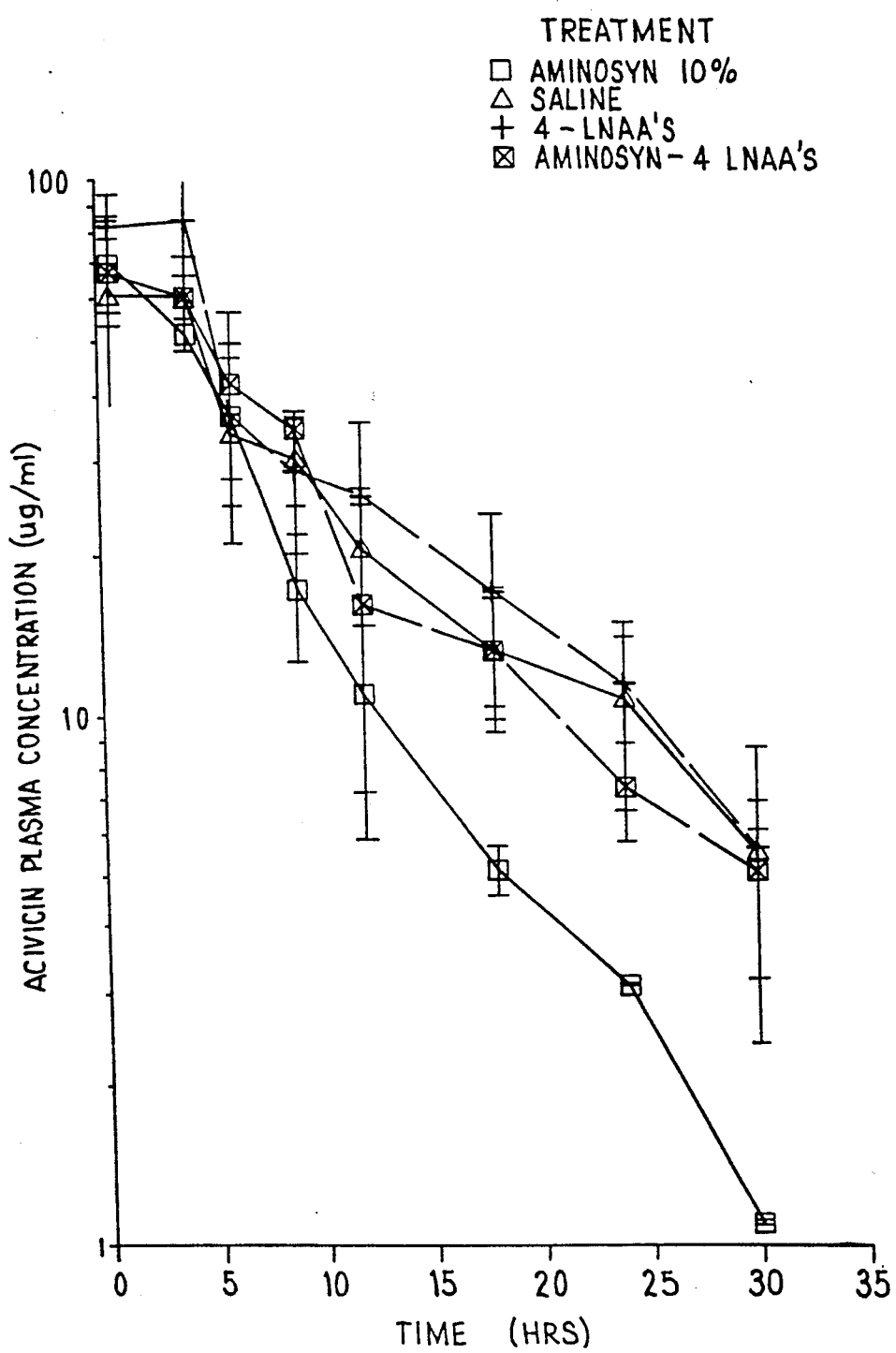

Acivicin's dose-limiting toxicity is neurotoxicity which is dose-dependent and reversible. In more severely affected patients in previous Phase I and II trials, the symptoms were disabling and required discontinuation of treatment. Efficacy of acivicin in clinical trials conducted to date has been marginal. Laboratory data indicate a strong dependence of acivicin cytotoxicity on tumor cell exposure concentration and duration. By raising doses in cancer patients above what is currently tolerable, better efficacy is obtained.

Using our cat model, we showed that an infusion of Aminosyn 10% reduced the levels of acivicin in the brain significantly and prevented some of the signs of acivicin toxicity seen in the cat model (ataxia, sedation). Acivicin's efficacy in tumor-bearing mice does not appear to be ablated by Aminosyn co-treatment (5,6). Preliminary findings from a Phase I trial suggest that the volume of Aminosyn which must be administered is a problem, especially when infused via a peripheral vein. There is also some concern about the total nitrogen load administered in Aminosyn. We have determined that a simpler combination of amino acids (which could be administered in a lower infusion volume) has the same toxicity-preventive effect as Aminosyn, but offers certain advantages thereover.

EXPERIMENT 1

(a) Materials and Methods

(i) Animals

Female cats, ranging in weight from 2.4 to 3.2 kg. were housed singly. Food and water were given ad libitum except for a fasting period from four hours pre-drug administration to 18 hours post-drug administration when only water was available. All cats had dual chronic jugular cannulas placed surgically for infusion and blood sampling as described previously (4). The cats were anaesthetized using a combination of Rompun ® and sodium pentobarbital instead of pentobarbital alone. This allowed the use of a smaller amount of sodium pentobarbital and resulted in a more rapid recovery from anaesthesia.

(ii) Agents

Acivicin was prepared by fermentation, isolated and characterized at The Upjohn Company by published methods. Aminosyn 10% was purchased from Abbott Laboratories, North Chicago, IL. Aminosyn is a sterile amino acid solution with electrolytes for intravenous infusion. Composition of Aminosyn 10% is given in Table I. A large neutral amino acid solution (LNAA) and a solution of other amino acids (OAA) were prepared from crystalline amino acids (sources given in Table 2) dissolved in sterile water for irrigation (McGaw, Irvine, CA) and sterile-filtered using Gelman Acrodisc or Millipore Millex 0.22 μm filter units. The composition of these two amino acid solutions is given in Table 2. The concentrations of the individual amino acids in these solutions were the same as in Aminosyn 10%. Saline-infused cats received 0.9% sodium chloride irrigation, USP (McGaw, Irvine, CA).

(b) Experimental Design

Cats were administered saline, Aminosyn, LNAA or OAA by constant rate infusion into the catheterized jugular vein. Solutions were infused by means of a Harvard Model 960 infusion pump (Milford, MA) operating at 21 ml/hr. Solutions were contained in Becton-Dickinson 50 ml plastic syringes fitted with Milipore Millex or Gelman Acrodisc 0.22 μm filters for sterilization. Syringes were refilled with solutions at 2.5 hour intervals throughout the experiment. The filter was attached to a swivel atop the cage via a plastic tubing adapter and a length of PE60 tubing. The reinforced end of the cannula in the cat was attached to the swivel via a 5 mm long 26 gauge stainless steel connector and the "slinky" line (5) or in some uncooperative cats, 112 cm of PE60 tubing protected by a flexible metal tether. The infusion was started four hours prior to i.p. injection of acivicin at 60 mg/kg. Infusions were continued for 18 hours after the acivicin dose except for a five minute interval at +12 hours when cats were disconnected from the infusion apparatus for ataxia testing and observation of other symptoms.

Blood was sampled through the blood sampling cannula at −4.0, 0, +4, +6, +9, +12, +18, +24 and +30 hours relative to the acivicin dose, for determination of acivicin concentration by microbiological assay.

Cats were judged to be ataxic or normal by observing if they could walk along the edge of an upended wooden pallet without falling. Sedation and somnolence were determined by observing the animals' behavior upon approach to the cage by experimenters. Cats were observed for behavioral changes throughout the experimental period. Somnolence, sedation and ataxia were evaluated at −4, +12, +18 and +24 hours.

The experiment was originally designed so that those cats receiving Aminosyn or LNAA would receive either normal saline or NEAA, respectively, two weeks later. However, due to the deaths of two cats (B and C) during the washout period due to infection with beta-hemolytic streptococcus, two replacement cats were prepared and given the cross-over infusions. Another cat (A) died of unknown causes during its second infusion (Aminosyn) and was not replaced.

(c) Results and Discussion

Detailed observations on each experimental animal are recorded in the Appendix. Table 3 shows the effect of saline or amino acid co-treatment on the incidence of toxic symptoms in the acivicin-treated cats. As seen previously, mydriasis was not alleviated by the Aminosyn infusion nor by any of the other infusions. Like the Aminosyn-treated cats, the LNAA-treated cats exhibited neither ataxia nor sedation. The saline- and OAA-treated cats were both ataxic sedated.

The plasma levels of acivicin in cats infused with the various mixtures are shown graphically in FIG. 1. The plasma pharmacokinetic calculations are given in Table 4. Although the mean values of t1/2 and Cl in the saline and Aminosyn groups were quite comparable to what was observed in the previous study (8) and indicated that Aminosyn enhanced acivicin clearance, these differences were not statistically significant due to the low number of cats in which data was analyzed. The pharmacokinetic data in LNAA- and OAA-treated cats were very similar to the data in the saline-treated animals. This result suggests that LNAA treatment could prevent CNS toxicity by blocking brain uptake without increasing acivicin total body clearance.

We have shown that an infusion of large neutral amino acids was as effective as the Aminosyn infusion at preventing acivicin-induced ataxia and sedation in cats. These data support the hypothesis that acivicin transport into the brain occurs by means of the large neutral amino acid transport system. The total body clearance of acivicin in cats treated with the large neutral amino acid infusion was apparently not increased as was seen with the Aminosyn infusion. This result suggests that not only could a large neutral amino acid infusion be as effective at reducing or eliminating toxic symptoms of acivicin treatment but could have the added advantage of not increasing the total body clearance of acivicin.

TABLE 1

The Aminosyn Family
(Abbott Laboratories, North Chicago, IL 60066)
The Aminosyn family is comprised of sterile, non-pyrogenic solutions of crystalline amino acids for intravenous infusion. They are used with dextrose or dextrose and lipid emulsion for parenteral nutrition. The Aminosyn family is a highly adaptable family which can satisfy the nutritional requirements for protein synthesis in patients who cannot be fed orally, be those needs -
peripheral vein-nutritional maintenance
total parenteral nutrition for the pediatric patient
total parenteral nutrition for the metabolically stable adult patient
total parenteral nutrition for the hypermetabolic patient
total parenteral nutrition for the renal patient.

|  | 3.5% | 3.5%* | 5% | 7% | 7% w/Electro |
|---|---|---|---|---|---|
| Amino Acids (mg/100 ml) |  |  |  |  |  |
| L-Isoleucine | 252 | 252 | 360 | 510 | 510 |
| L-Leucine | 329 | 329 | 470 | 660 | 660 |
| L-Lysine[a] | 252 | 252 | 360 | 510 | 510 |
| L-Methionine | 140 | 140 | 200 | 280 | 280 |
| L-Phenylalanine | 154 | 154 | 220 | 310 | 310 |
| L-Threonine | 182 | 182 | 260 | 370 | 370 |
| L-Tryptophan | 56 | 56 | 80 | 120 | 120 |
| Valine | 280 | 280 | 400 | 560 | 560 |
| Non-essential Amino Acids |  |  |  |  |  |
| L-Alanine | 448 | 448 | 640 | 900 | 900 |
| L-Arginine | 343 | 343 | 490 | 690 | 690 |
| L-Histidine[b] | 105 | 105 | 150 | 210 | 210 |
| L-Proline | 300 | 300 | 430 | 610 | 610 |
| L-Serine | 147 | 147 | 210 | 300 | 300 |
| L-Tryosine | 31 | 31 | 44 | 44 | 44 |
| Glycine (Aminoacetic Acid, USP) | 448 | 448 | 640 | 900 | 900 |

|  | 3.5% | 3.5% M | 5% | 7% | 7% w/Electro |
|---|---|---|---|---|---|
| Electrolytes (mEq/liter) |  |  |  |  |  |
| Sodium (Na+) | 7[c] | 47[c] | none | none | 70 |
| Potassium (K+) | none | 13 | 5.4[d] | 5.4[d] | 66[d] |
| Magnesium (Mg++) | none | 3 | none | none | 10 |
| Phosphorus (P)[e] | none | 3.5 (mM) | none | none | 30 (mM) |
| Chloride (Cl−) | none | 40 | none | none | 96 |
| Acetate | 46[g] | 58[h] | 86[g] | 105[g] | 124[g] |
| Protein Equivalent (approx. g/l) | 35 | 35 | 50 | 70 | 70 |
| Total Nitrogen (g/l) | 5.5 | 5.5 | 7.86 | 11.00 | 11.00 |
| Osmolarity (mOsm/l)(Calc) | 357 | 477 | 500 | 700 | 1013 |
| pH (Approx.) | 5.3[i] | 5.3[i] | 5.3[i] | 5.3[i] | 5.3[i] |

TABLE 1-continued

The Aminosyn Family
(Abbott Laboratories, North Chicago, IL 60066)
The Aminosyn family is comprised of sterile, non-pyrogenic solutions of crystalline amino acids for intravenous infusion. They are used with dextrose or dextrose and lipid emulsion for parenteral nutrition. The Aminosyn family is a highly adaptable family which can satisfy the nutritional requirements for protein synthesis in patients who cannot be fed orally, be those needs -
  peripheral vein-nutritional maintenance
  total parenteral nutrition for the pediatric patient
  total parenteral nutrition for the metabolically stable adult patient
  total parenteral nutrition for the hypermetabolic patient
  total parenteral nutrition for the renal patient.

| | 8.5% | 8.5% w/electro | 10% | RF-5.2% |
|---|---|---|---|---|
| Amino Acids (mg/100 ml) | | | | |
| Essential Amino Acids | | | | |
| L-Isoleucine | 620 | 620 | 720 | 462 |
| L-Leucine | 810 | 810 | 940 | 726 |
| L-Lysine[a] | 624 | 624 | 720 | 535 |
| L-Methionine | 340 | 340 | 400 | 726 |
| L-Phenylalanine | 380 | 380 | 400 | 726 |
| L-Threonine | 460 | 460 | 520 | 330 |
| L-Trytophan | 150 | 150 | 160 | 165 |
| L-Valine | 680 | 680 | 800 | 528 |
| Non-essential Amino Acids | | | | |
| L-Alanine | 1100 | 1100 | 1280 | None |
| L-Arginine | 50 | 850 | 980 | 600 |
| L-Histidine[b] | 260 | 260 | 300 | 429 |
| L-Proline | 750 | 750 | 860 | none |
| L-Serine | 370 | 370 | 420 | none |
| L-Tyrosine | 44 | 44 | 44 | none |
| Glycine (Aminoacetic Acid, USP) | 1100 | 1100 | 1280 | none |
| Electrolytes (mEq/liter) | | | | |
| Sodium (Na+) | none | 70 | none | none |
| Potassium (K+) | 5.4[d] | 6.6[d] | 5.4[d] | 5.4[d] |
| Magnesium (Mg++) | none | 10 | none | none |
| Phosphorus (P)[e] | none | 30 (mM) | none | none |
| Chloride (Cl-) | 35 | 142[g] | 148[g] | 105[g] |
| Protein Equivalent (approx. g/l) | 85 | 85 | 100 | 52 |
| Total Nitrogen (g/l) | 13.4 | 13.4 | 15.72 | 7.87 |
| Osmolarity (mOsm/l) (Calc) | 850 | 1160 | 1000 | 475 |
| pH (Approx) | 5.3[i] | 5.3[i] | 5.3[i] | 5.3[i] |

*Contains maintenance electrolytes
[a]Amount cited is for L-Lysine alone and does not include the acetate salt
[b]Histidine is considered essential for patients in renal failure
[c]Includes 7 mEq Na+/liter from the antioxidant, sodium hydrosulfite
[d]Includes 5.4 mEq K+ liter/from the antioxidant, potassium metabisulfite
[e]mM = millimoles; one mM of phosphorus = 31 mg phosphorus
[f]Includes approximately 18 mEq/liter from HCl used in pH adjustment
[g]Includes acetic acid used in processing and acetate from L-Lysine
[h]Includes acetic acid used in processing and the acetate salts of potassium, magnesium and L-Lysine
[i]Adjusted with acetic acid
[j]Adjusted with acetic acid and hydrochloric acid

TABLE 2

Composition of Solutions (mg/100 ml) Containing the Four Large Neutral Amino Acids (LNAA) or the Other Amino Acids (OAA) Formulated in Aminosyn ®, 10%

| LNAA | |
|---|---|
| L-isoleucine (Sigma) | 720 |
| L-leucine (Aldrich) | 940 |
| L-phenylalanine (Nutritional Biochemicals) | 400 |
| L-valine (Sigma) | 800 |
| pH adjusted to 5.3 with glacial acetic acid. Calculated osmolarity, 220 mOSM | |
| OAA | |
| DL-alanine (Aldrich) | 1280 |
| L-Arginine (Nutritional Biochemicals) | 980 |
| L-Histidine (ICN) | 300 |
| L-proline (ICN) | 860 |

TABLE 2-continued

Composition of Solutions (mg/100 ml) Containing the Four Large Neutral Amino Acids (LNAA) or the Other Amino Acids (OAA) Formulated in Aminosyn ®, 10%

| | |
|---|---|
| L-serine (ICN) | 420 |
| L-tryosine (NUtritional Biochemicals) | 44 |
| glycine (ICN) | 1280 |
| pH adjusted to 5.3 with NaOH. Calculated osmolarity, 507 mOSM. | |

TABLE 3

Effect of Saline or Amino Acid Mixture Co-Treatment on Incidence of Toxic Symptoms in Acivicin-Treated Cats

| | Saline | Aminosyn | LNAA | OAA |
|---|---|---|---|---|
| mydriasis | 4/4 | 3/3 | 4/4 | 4/4 |
| vomiting | 1/4 | 0/3 | 0/4 | 2/4 |
| sedation | 4/4 | 0/3 | 0/4 | 4/4 |
| ataxia | 4/4 | 0/3 | 0/4 | 4/4 |

TABLE 4

Acivicin Pharmacokinetic Data in Cats Administered a Concomitant Infusion of Saline, Aminosyn, LNAA or OAA (mean ± s.d.)[a]

| Treatment | n | K (hr$^{-1}$) | t½ (hr) |
|---|---|---|---|
| Aminosyn | 2 | 0.16 ± 0.03 | 4.3 ± 0.7 |
| Saline | 3 | 0.087 ± 0.027 | 8.4 ± 2.5 |
| LNAA | 3 | 0.084 ± 0.01 | 8.3 ± 0.8 |
| OAA | 3 | 0.095 ± 0.014 | 7.4 ± 1.06 |
| saline | 4 | 0.275 ± 0.046 | 2.6 ± 0.41 |
| aminosyn | 4 | 0.093 ± 0.028 | 8.18 ± 1.36 |

| Treatment | n | Cl (ml/hr/kg) | Varea (ml/kg) |
|---|---|---|---|
| Aminosyn | 2 | 110 ± 8 | 684 ± 64 |
| Saline | 3 | 77 ± 20 | 893 ± 143 |
| LNAA | 3 | 63 ± 10 | 750 ± 81 |
| OAA | 3 | 77 ± 6 | 814 ± 61 |
| saline | 4 | 110.93 ± 15.7 | 407.6 ± 33.1 |
| Aminosyn | 4 | 55.08 ± 8.77 | 625.2 ± 12.3 |

[a]Blood draws were unsuccessful in several cats, resulting in only 2-3 sets of plasma levels/treatment which were complete enough for pharmacokinetic analysis.

We claim:

1. A method for the prevention of CNS toxicity of acivicin in animals which comprises the concomitant administration of acivicin and an amino acid solution consisting essentially of one or any combination of the large amino acids valine, leucine, isoleucine or phenyl alamine in concentrations of 100 to 1000 mg/ml.

2. A method according to claim 1 wherein the amino acid solution consists essentially of L-isoleucine, L-leucine, L-phenylalanine and L-valine.

3. A method according to claim 1 wherein acivicin and the amino acid solution are administered orally.

4. A method according to claim 1 wherein acivicin and the amino acid solution are administered orally.

5. A method according to claim 2 wherein acivicin and the amino acid solution are administered orally.

6. A method according to claim 1 wherein acivicin and the amino acid solution are administered intravenously.

7. A method according to claim 1 wherein acivicin and the amino acid solution are administered intravenously.

8. A method according to claim 2 wherein acivicin and the amino acid solution are administered intravenously.

9. A method according to claim 1 wherein the time of administration of amino acid relative to acivicin is from 30 minutes to eight hours prior to acivicin administration and continuing for eight hours to seven days after.

10. A method according to claim 1 wherein the time of administration of amino acid relative to acivicin is from 30 minutes to eight hours prior to acivicin administration and continuing for eight hours to seven days after.

11. A method according to claim 2 wherein the time of administration of amino acid relative to acivicin is from 30 minutes to eight hours prior to acivicin administration and continuing for eight hours to seven days after.

12. A method for the prevention of central nervous system toxicity of acivicin which comprises the concomitant intravenous administration of acivicin and an amino acid solution consisting essentially of large neutral amino acids wherein the time of administration of amino acid solution relative to acivicin is from 30 minutes to eight hours prior to acivicin administration and continuing for eight hours to seven days after.

13. A method according to claim 12 wherein the amino acid solution contains one or any combination of the large amino acids valine, leucine, isoleucine or phenylalanine at concentrations of 100 to 1000 mg/ml.

14. A method according to claim 13 wherein the amino acid solution consists essentially of L-isoleucine, L-leucine, L-phenylalanine and L-valine.

15. An amino acid solution consisting essentially of any combination of the large amino acids valine, leicene, isoleucine or phenylamine in concentrations of 100 to 1000 mg/ml.

* * * * *